Jan. 27, 1959 R. L. BYRUM Plant Pat. 1,804
ROSE PLANT
Filed June 16, 1958
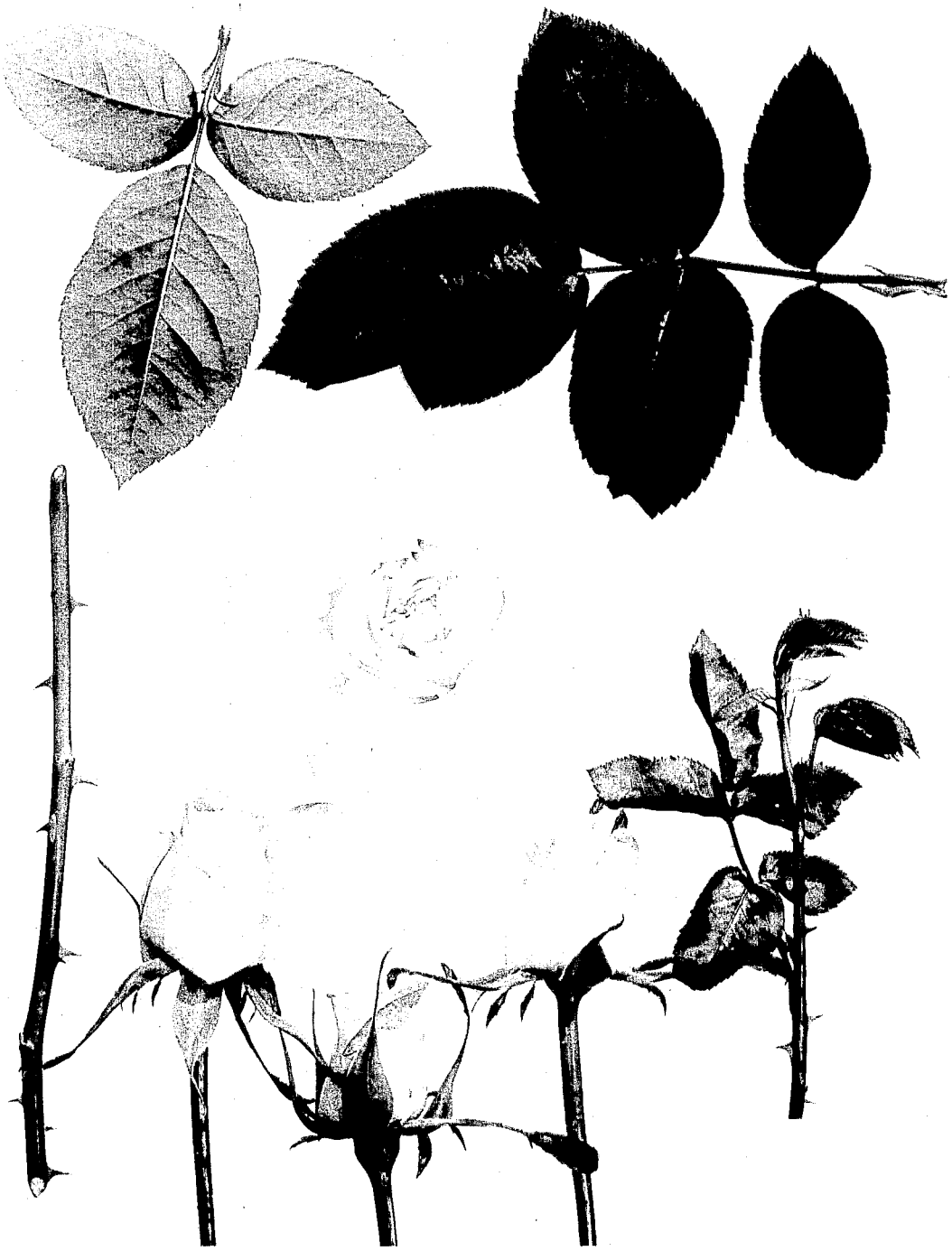
INVENTOR
R. L. Byrum
BY Robb & Robb
ATTORNEYS United States Patent Office Plant Pat. 1,804
Patented Jan. 27, 1959

1,804

ROSE PLANT

Roy L. Byrum, Richmond, Ind., assignor to Joseph H. Hill Company, Richmond, Ind., a corporation of Indiana Application June 16, 1958, Serial No. 742,454

1 Claim. (Cl. 47—61)

The present invention relates to a new and distinct variety of rose plant of the hybrid tea class, which was originated by me by crossing the variety "Peace" (Plant Patent No. 591) with the variety "Yellow Perfection" (Plant Patent No. 1,083).

The primary objective of this breeding was to produce a new rose variety which bears blooms of a color comparable to those of "Peace," but combined with a longer bud form and with a petalage at least as great as that of "Peace." This objective was fully achieved, along with other improvements, as evidenced by the following unique combination of features which are outstanding in the new variety, and which distinguish it from its parents as well as from all other varieties of which I am aware:

(1) Abundant dark green, semi-glossy foliage borne on almost the entire length of the stem;

(2) A habit of bearing flowers on strong stems of a length suitable for cut flowers;

(3) Relatively long buds;

(4) A distinctive Mimosa Yellow general color tonality of the flowers; and (5) Suitability for greenhouse forcing use.

In comparison with the seed parent, "Peace," the new variety bears flowers which sometimes have even more color than this parent, particularly in the bud and half-open flower stages, and the bud is usually longer than that of "Peace."

As compared with the pollen parent, "Yellow Perfection," the new variety has a substantially greater flower petalage, and the foliage is glossier and more abundant so that it covers almost the entire length of the stem.

Asexual reproduction of my new variety, by grafting, as performed at Richmond, Indiana, and also by budding, as performed at West Grove, Pennsylvania, shows that the aforementioned characteristics and distinctions come true to form and are established and transmitted through succeeding propagations.

The accompanying drawing shows typical specimens of the vegetative growth and flowers of my new variety, in different stages of development and as depicted in color as nearly true as it is reasonably possible to make the same in a color illustration of this character.

The following is a detailed description of my new variety, with color terminology in accordance with Robert F. Wilson's Horticultural Colour Chart (hereinafter abbreviated as "Wilson"), Ridgway's Color Standards and Nomenclature (hereinafter abbreviated as "Ridgway"), and Koster's Color Guide (hereinafter abbreviated as "Koster"), as indicated:

Type: Greenhouse; bush; seedling.
Class: Hybrid tea.
Breeding: Seedling.
*Seed parent.*—"Peace."
*Pollen parent.*—"Yellow Perfection."
Propagation: Holds its distinguishing characteristics through succeeding propagations by both grafting and budding.

*Flower*

Locality where grown and observed: Richmond, Indiana.
Flowers borne: One to stem; on long, strong stems.
Quantity of bloom: Abundant, in greenhouse.
Continuity: Continuous.
Fragrance: Moderate. Nature—tea.

Bud:

*Peduncle.* — Medium length; medium diameter; strong; erect. Bark—smooth; color—Spinach Green, Plate 0960/3 (Wilson), with part of peduncle overlaid with Dark Violet, Plate #58 (Koster). Thorns—none. Prickles—numerous; color—some Dark Violet, Plate #58 (Koster), and some Pod Green, Plate 061/3 (Wilson). Hairs—none.

*Before calyx breaks.*—Size—medium large. Form—short pointed; ovoid; with a conspicuous neck; with foliaceous appendages on the surface of the bud; with stout foliaceous parts extending beyond the tip of the bud equal to ¾ or more of its length. Color—Lettuce Green, Plate 861/1 (Wilson).

*As calyx breaks.*—Color—outside of petal—Citron Green, Plate 763 (Wilson), with very light veins of Pod Green, Plate 061 (Wilson).

*As first petal opens.*—Size—large. Form—long pointed; ovoid. Color: outside—Aureolin, Plate 3/1 (Wilson); inside—Aureolin, Plate 3 (Wilson).

*Opening.*—Opens up well in greenhouse; no unusual characteristics attributed to weather conditions.

Bloom:

*Size (when fully open).*—Large; from 4 to 4½ inches.

*Petalage.*—Very double; from 55 to 60 petals; arranged irregularly.

*Form.*—Full and high-centered at first, but becoming open; petals at first being tightly cupped, but later becoming loosely rolled outward at maturity.

Petals:

*Texture.*—Thick; leathery. Inside—satiny. Outside—satiny.

*Shape.*—Outside petals obovate, with apex obtuse. Intermediate petals—obovate, with apex obtuse. Inside petals—some obovate and some spatulate, with apex obtuse.

This description of a newly opened flower was made from a rose grown in a greenhouse in the month of December, at Richmond, Indiana:

*Color.*—Outer petals: outside surface—Mimosa Yellow, Plate 602/1 (Wilson); inside surface—Mimosa Yellow, Plate 602/3 (Wilson) at top of petal, changing through Mimosa Yellow, Plate 602/2 (Wilson) to Mimosa Yellow, Plate 602/1 (Wilson) at base of petal. Intermediate petals: outside surface—Mimosa Yellow, Plate 602/2 (Wilson); inside surface—Mimosa Yellow, Plate 602/1 (Wilson). Inner petals: outside surface—Mimosa Yellow, Plate 602/2 (Wilson); inside surface—Mimosa Yellow, Plate 602/1 (Wilson).

This description was made from a rose that was open for 3 days in a greenhouse in the month of December, at Richmond, Indiana:

*Color.*—Outer petals: outside surface—Mimosa Yellow, Plate 602/3 (Wilson), shading to Mimosa Yellow, Plate 602/2 (Wilson) at base; inside surface—Mimosa Yellow, Plate 602/3 (Wilson), shading through Mimosa Yellow, Plate 602/2 (Wilson) to Mimosa Yellow, Plate 602/1 (Wilson) at base; some petals lightly tinted with Violet Rose, Plate #39 (Koster). Intermediate petals: outside surface—Mimosa Yellow, Plate 602/3 (Wilson) shading to Mimosa Yellow, Plate 602/2 (Wilson), at base; inside surface—Mimosa Yellow, Plate 602/3 (Wilson), shading through Mimosa Yellow, Plate 602/2 (Wilson) to Mimosa Yellow, Plate 602/1 (Wilson) at base. Inner petals: outside surface—Mimosa Yellow, Plate 602/2 (Wilson); inside surface—Mimosa Yellow, Plate 602/2 (Wilson), shading to Mimosa Yellow, Plate 602/3 (Wilson) at base of petals.

*General color effect.*—Newly opened flower—Mimosa Yellow, Plate 602/1 (Wilson). 3-days open—from Mimosa Yellow, Plate 602/2 (Wilson) to Mimosa Yellow, Plate 602 (Wilson).

*Behavior.*—Persist, but when cut and kept in water, petals drop off after several days; fading to Mimosa Yellow, Plate 602/3 (Wilson).

*Flower longevity.*—Cut roses grown in greenhouse and kept at living-room temperatures—4 or 5 days in November.

*Reproductive organs*

Stamens: Many; arranged regularly about pistils.

Filaments: Medium length; few without anthers. Color—some are Cream-Yellow, Plate #4 (Koster), and some are a mixture of Cream-Yellow, Plate #4 (Koster) and Amaranth Red, Plate #43 (Koster).

Anthers: Medium large; all open at once. Color—Cream-Yellow, Plate #4 (Koster).

Pollen: Sparse. Color—Orange Cadmium, Plate #10 (Koster).

Pistils: Medium number.

Styles: Uneven; short; moderately thin; bunched. Color—a mixture of Cream-Yellow, Plate #4 (Koster) and French Purple, Plate #42 (Koster).

Stigma: Color—Sulphury White, Plate #3 (Koster).

Ovularies: Most encased in, but a few protruding from calyx.

Hips: None developed.

Sepals: Permanent; long; spear-shaped. Color: inside—Scheeles Green, Plate 860 (Wilson), overlaid with white fuzz; outside—Scheeles Green, Plate 860 (Wilson).

Seeds: None developed.

*Plant*

Foliage:

*Leaves.*—Compound of 3–5–7 leaflets; abundant; medium large; heavy; glossy; leathery.

*Leaflets.*—Shape—ovoid. Apex—acute. Base—round. Margin—simply serrate.

*Color.*—Mature: upper surface—near Empire Green, Plate XXXII (Ridgway); under surface—near Chromium Green, Plate XXXII (Ridgway). Young: upper surface—near Cress Green, Plate XXXI (Ridgway); under surface—near Light Cress Green, Plate XXXI (Ridgway).

*Rachis (the supporting stem of the compound leaf).*—Heavy. Upper side—grooved. Under side—sparsely thorny.

*Stipules.*—Moderately short; moderately narrow; with points of medium length and some turning out more and others less than 45°.

Growth:

*Habit.*—Bush; upright; much-branched.

*Growth.*—Free; vigorous.

*Canes.*—Large diameter.

*Main stems.*—Color—some Cedar Green, Plate #80 (Koster), and some Cedar Green, Plate #80 (Koster), overlaid with Tobacco Brown, Plate #88 (Koster). Thorns—several; medium length; hooked downward; with long, narrow base; color—Bistre, Plate #93 (Koster). prickles—very few; color—Bistre, Plate #93 (Koster). Hairs—none.

*Branches.*—Color—Scheeles Green, Plate 860/3 (Wilson) with some parts overlaid with Dark Violet, Plate #58 (Koster). Thorns—several; long; hooked downward; with long, narrow base; color—Deep Hellebore Red, Plate XXXVIII (Ridgway). Prickles—few; color—Deep Hellebore Red, Plate XXXVIII (Ridgway). Hairs—none.

*New shoots.*—Color—partly Lettuce Green, Plate 861/3 (Wilson), with remainder Lettuce Green, Plate 861/3 (Wilson), overlaid with Oxblood Red, Plate 00823/3 (Wilson). Thorns—many; medium length; hooked downward; with long, narrow base; color—Amaranth Red, Plate #43 (Koster), with tips Creamy White, Plate #2 (Koster). Prickles—few; color—Amaranth Red, Plate #43 (Koster). Hairs—none.

I claim:

A new and distinct variety of rose plant of the hybrid tea class, substantially as herein shown and described, characterized particularly as to novelty by the unique combination of abundant dark green, semi-glossy foliage borne on almost the entire length of the stem, a habit of bearing flowers on strong stems of a length suitable for cut flowers, relatively long buds, a distinctive Mimosa Yellow general color tonality of the flowers, and a suitability for greenhouse forcing use.

No reference cited.